US009741529B2

(12) United States Patent
Mele et al.

(10) Patent No.: US 9,741,529 B2
(45) Date of Patent: Aug. 22, 2017

(54) MICRO-CHAMBER FOR INSPECTING SAMPLE MATERIAL

(71) Applicant: FEI Company, Hillsboro, OR (US)

(72) Inventors: Luigi Mele, Eindhoven (NL); Pleun Dona, Veldhoven (NL); Gerard Nicolaas Anne van Veen, Waalre (NL)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 15/221,510

(22) Filed: Jul. 27, 2016

(65) Prior Publication Data
US 2017/0032928 A1  Feb. 2, 2017

(30) Foreign Application Priority Data

Jul. 29, 2015 (EP) ..................................... 15178825

(51) Int. Cl.
H01J 37/20 (2006.01)
H01J 37/26 (2006.01)
G01N 1/04 (2006.01)
G01N 1/28 (2006.01)

(52) U.S. Cl.
CPC ................ H01J 37/20 (2013.01); G01N 1/04 (2013.01); H01J 37/26 (2013.01); H01J 2237/2003 (2013.01); H01J 2237/2005 (2013.01)

(58) Field of Classification Search
USPC ........ 435/4, 7.93–7.95, 283.1, 286.5, 287.1, 435/287.2, 288.5, 288.6, 288.7, 290.4; 422/50, 81, 82.05, 502–504, 550, 551, 422/561, 563, 940, 946, 947; 430/138, 430/149; 205/334, 335
See application file for complete search history.

(56) References Cited

U.S. PATENT DOCUMENTS 5,344,611 A  9/1994 Vogler et al.
5,406,087 A  4/1995 Fujiyoshi et al.
(Continued)

FOREIGN PATENT DOCUMENTS

EP   2722566 B1   5/2015
WO   2006031104 A1   3/2006

OTHER PUBLICATIONS

Creemer, J.F., et al., "An all-in-one nanoreactor for high-resolution microscopy on nanomaterials at high pressures", Jan. 23-27, 2011, 4 pages, IEEE, Cancun, Mexico.
(Continued)

Primary Examiner — Bernard Souw
(74) Attorney, Agent, or Firm — Scheinberg & Associates, P.C.; Michael O. Scheinberg

(57) ABSTRACT

A micro-chamber for inspecting sample material can be filled with sample material immersed in a liquid without the need of applying vacuum tubing's to the micro-chamber. The micro-chamber includes an inspection volume for holding the sample material for observation. The inspection volume is defined by a first rigid layer, a second rigid layer spaced from the first rigid layer, and a hermetic seal between the first and the second rigid layers. One of the rigid layers includes thin part can be punctured. The liquid with immersed sample material, when placed upon the thin part, is sucked into the evacuated inspection volume when the thin part is punctured.

20 Claims, 2 Drawing Sheets

(56) References Cited

U.S. PATENT DOCUMENTS

Figure 1:
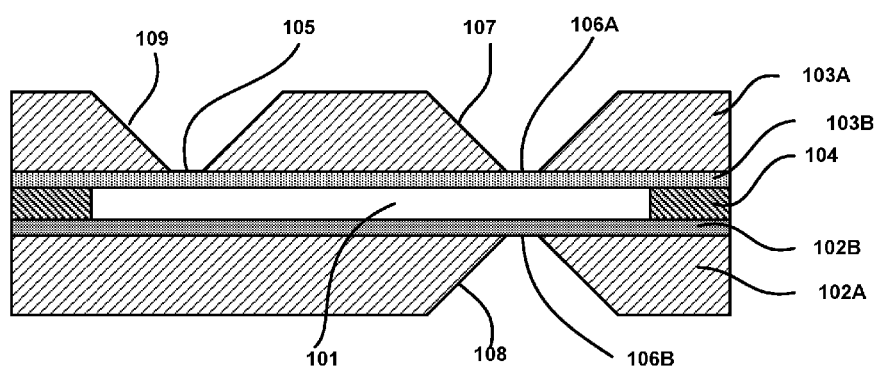

| | | | | |
|---|---|---|---|---|
| 5,705,018 | A * | 1/1998 | Hartley | F04B 43/043 |
| | | | | 156/345.1 |
| 8,642,323 | B2 * | 2/2014 | Sharpin | C12Q 1/08 |
| | | | | 422/82.05 |
| 8,894,946 | B2 * | 11/2014 | Nielsen | C12Q 1/68 |
| | | | | 422/131 |
| 8,986,983 | B2 * | 3/2015 | Montagu | B01L 3/502715 |
| | | | | 422/504 |
| 9,260,740 | B2 * | 2/2016 | Sharpin | C12Q 1/08 |
| 2006/0275852 | A1 * | 12/2006 | Montagu | B01L 3/502715 |
| | | | | 435/7.93 |
| 2008/0179518 | A1 | 7/2008 | Creemer et al. | |
| 2011/0272290 | A1 * | 11/2011 | Dasgupta | G01N 33/1813 |
| | | | | 205/335 |
| 2012/0115216 | A1 * | 5/2012 | Sharpin | C12Q 1/08 |
| | | | | 435/288.7 |
| 2013/0115607 | A1 * | 5/2013 | Nielsen | C12Q 1/68 |
| | | | | 435/6.12 |
| 2015/0136604 | A1 * | 5/2015 | Nielsen | B01L 3/502715 |
| | | | | 204/453 |

OTHER PUBLICATIONS

Marton, L., "Electron Microscopy of Biological Objects", Nature 133 (1934), p. 911.

Mele, L., et al., "Wafer-level assembly and sealing of a MEMS nanoreactor for in situ microscopy", Journal of Micromechanics and Microengineering, Jul. 22, 2010, pp. 1-9, vol. 20, No. 8, 2010 IOP Publishing Ltd.

* cited by examiner

MICRO-CHAMBER FOR INSPECTING SAMPLE MATERIAL

The invention relates to a micro-chamber for inspecting sample material, the sample material immersed in a liquid when filling the micro-chamber, the micro-chamber comprising:

An inspection volume for holding the sample material, the inspection volume defined by:
 a first rigid layer,
 a second rigid layer spaced from the first rigid layer, and
 a hermetic seal between the first and the second rigid layer.

Such a micro-chamber is known from International Application Publication No. WO006031104A1. Said publication describes a microreactor for use in a microscope, comprising a first and second rigid layer, the rigid layers both at least locally transparent to an electron beam of an electron microscope, and extending next to each other at a mutual distance from each other and between which an inspection volume is enclosed. The separation of the rigid layers (here also named "chips" or "wafers") is typically less than 10 µm, and may well be in the tens of nanometer range.
The micro-chamber further has an inlet and an outlet to feed sample material to the inspection volume.

A disadvantage of said micro-reactor is that for filling the inspection volume with a liquid with immersed sample material, a connection between the inlet and a supply of liquid must be made, and a connection between the outlet and a vacuum pump must be made.
It is noted that sometimes the capillary forces are sufficient, but this depends on the liquid, the amount of sample material in the suspension, etc. It is thus something that cannot be relied on.
As the size of the micro-chamber is small (typically less than $3 \times 3$ mm$^2$), making a reliable connection is difficult, resulting in a time consuming process.

It is an object of the invention to provide an innovative micro-reactor. More specifically, it is an object of the invention that this micro-reactor is to be filled with sample material without earlier mentioned draw-backs.

These and other objects are achieved by the micro-reactor as set forth in the opening paragraph above, the micro-reactor characterized in that, prior to filling the inspection chamber with the liquid with immersed sample material,
 A thin part of at least one rigid layer separates the inspection volume from the outside,
 The thin part is equipped to be punctured, and
 The inspection volume is an evacuated volume,
as a result of which the liquid and immersed sample material, when placed upon the thin part, is sucked into the inspection volume when the thin part is punctured.

It is noted that in this context an immersion of sample material includes suspensions, emulsions and colloids. Where 'inspection' is used, this is a synonym for 'observation'.

By pre-evacuating the inspection volume and then puncturing the thin part the liquid with immersed sample material is sucked in the inspection volume without relying on capillary forces or needing an external pump connection. Puncture of a thin part is easy, and also manufacturing such a thin part is—when using semi-conductor techniques—not difficult, as will be shown later. Therefore this micro-chamber offers a cheap, quick and reliable solution to the problem.

It is noted that L. Marton, "Electron Microscopy of Biological Objects", *Nature* 133 (1934), page 911 describes a micro-chamber where a sample is held between two aluminium films with a thickness of 0.5 µm each, the films clamped together. The use of films implies that the separation between the films is ill defined.

It is further noted that U.S. Pat. No. 5,406,087 describes a similar micro-chamber using two films, although here the thin films are preferable polymer films.

It is further noted that a micro-chamber similar to the micro-chamber described in WO2006031104A1 is described in "An all-in-one nanoreactor for high-resolution microscopy on nanomaterials at high pressures", J. F. Creemer et al., proceeding of MEMS 2011, Cancun, Mexico, Jan. 23-27, 2011, further referred to as Creemer [-1-]. Here a structure is built on a single silicon chip (the first rigid layer). On the chip first a sacrificial layer is formed, on which the other rigid layer is formed (the second rigid layer). After forming the second rigid layer the sacrificial layer is removed by a wet etch.
In the first rigid layer, the sacrificial layer and the second rigid layer holes are formed where needed, for example to seal or bond the first and the second rigid layer together, to provide inlet and outlet holes, to make transparent windows, to provide access holes needed for the wet etch, etc.
As one of the last steps the access holes are closed up by (locally) depositing a further layer of material.

It is mentioned that in "Wafer-level assembly and sealing of a MEMS nanoreactor for in situ microscopy", L. Mele et al., J. Micromech. Microeng. 20 (2010) 085040, further referred to as Mele [-2-], a micro-reactor is described that, during production, also comprises an evacuated chamber (see its FIG. 5(c)). However, the finished product has an opened inlet and an outlet (see FIG. 5(d)), and thereby this publication does not disclose a micro-reactor with an evacuated inspection volume.

In an embodiment the micro-chamber is equipped with a window transparent to radiation, as a result of which said radiation can enter and/or leave the inspection volume via this window.

The rigid layer may be transparent to the type of radiation used for inspecting the sample. If that is not the case, for example when using a window transparent to electrons, a window in the form of a recess can be formed, the recess or window transparent to electrons, while the rest of the rigid layer is less or not transparent to electrons, or a recess leaving only a thin membrane. This may be a membrane of, for example, silicon nitride in a recess in silicon, or such like.

It is noted that in this respect "transparent" is used when less than 10% of the radiation is scattered or absorbed when passing through the window, more preferably less than 1%.

In a further embodiment the micro-chamber is equipped with two windows transparent to radiation, one window in the first rigid layer and the second window in the second rigid layer, the windows positioned with respect to each other such, that radiation entering the inspection volume via one window can leave the inspection volume via the other window, thereby enabling transmissive inspection of the sample material.

By aligning the two windows such, radiation can pass through the two rigid layers.

In yet a further embodiment the radiation is radiation from the group of infrared light, visible light, ultra-violet light, X-ray, energetic electrons, neutrons, and the entrance window is transparent to said radiation.

By irradiating the sample with, for example, UV, fluorescence can be induced in the sample material. Preferably the windows are transparent to a wide range of radiation, but it is not excluded that the micro-chamber is equipped with an entrance window transparent to UV and an observation window transparent to visible light.

In another embodiment the hermetic seal is formed by an elastomer.

By sealing the two rigid layers to each other by means of an O-ring, a reliable seal is formed. The O-ring may be coated with a metal-oxide as described in, for example, European Patent No. EP2722566. The O-ring may be fitted in a recess in one or both rigid layers.

In yet another embodiment the hermetic seal is formed by bonding the first and the second rigid layer to each other.

By bonding the two rigid layers a hermetic seal is formed. Bonding is a technique well-known in semiconductor technology, thus enabling semiconductor processes for producing the micro-chambers. Bonding is also known as a method for connecting two glasses together, and can thus be used where glass substrates are used are rigid layers.

In yet another embodiment the first and the second rigid layer are spaced less than 10 μm from each other, preferably less than 2.5 μm.

The spacing of the micro-chambers described in Mele [-2-] is 2 μm, while the spacing of the micro-chambers described in Creemer [-1-] is, for example, 0.5 μm.

In an embodiment at least one of the rigid layers is a semiconductor chip.

The earlier mentioned micro-chambers described in WO2006031104A1 use two sandwiched semiconductor chips, while the micro-chambers described by Creemer [-1-] and Mele [-2-] use one semiconductor chip on which the second rigid layer is formed.

In an aspect of the invention a method of filling a micro-chamber according to the invention comprises the steps of:
  providing a micro-chamber according to any of the preceding claims,
  providing sample material immersed in a liquid,
  placing a droplet of the liquid with immersed sample material on the thin part of the micro-chamber,
  puncturing the thin part,
  inspecting the sample material.

In an embodiment of the method the step of puncturing the thin part is followed by a step of sealing the puncture.

Sealing the puncture is beneficial when evaporation of the liquid should be avoided. The liquid may be water, but also, for example, alcohol, or another liquid with a high evaporation rate. As sealant for example bee-wax can be used, or a glue like a cyanoacrylic glue, an epoxy, etc.

In another embodiment, prior to the step of inspecting the sample material, the liquid in which the sample material is immersed is evaporated.

When the sample material is to be inspected (as is the case in an electron microscope) in vacuum, it is beneficial to remove the liquid before inspection, as then the liquid cannot cause scattering of the radiation used for the inspection. Removing the liquid can be done by, for example, exposing the micro-chamber with punctured window for an extended time to vacuum. Also when the sample material is to be inspected in dry condition, the liquid should be removed. Evaporation can be achieved by exposing the micro-chamber to a vacuum, or by heating the micro-chamber.

It is noted that evaporation may also be preferred when inspection is performed in vacuum, to avoid that part of the liquid is pushed back as the thin part is exposed to the vacuum. As an alternative the thin part may be sealed again as mentioned earlier.

In another embodiment of the method inspection of the sample material comprises exposing the sample material to radiation from the group of infrared light, visible light, ultra-violet light, X-ray, energetic electrons, neutrons, and the window through which said radiation is admitted to the sample is transparent to said radiation.

In yet another embodiment of the method inspection of the sample material comprises detecting radiation emitted by the sample material, the radiation from the group of infrared light, visible light, ultra-violet light, X-ray, energetic electrons, neutrons, and the window through which said radiation is detected is transparent to said radiation.

It is noted that sometimes the radiation with which the sample is irradiated differs from the radiation detected. Examples are irradiation with UV light and detecting fluorescence induced by the UV, the fluorescence for example green (visible) light. Another such example is irradiation with electrons causing so-called cathode-luminescence, the cathode-luminescence being the emission of visible light to be detected.

In yet another embodiment the micro-chamber (and thus the sample material in the micro-chamber) is prior to inspection vitrified.

Vitrification is a process known as such in which biological samples are quickly cooled to cryogenic temperatures (below about 135 K). If the cooling is quick enough (order of magnitude $10^5$ K/s) amorphous ice is formed without ice crystals and thus without damage to the sample due to said ice crystals. High pressure freezing can be used to achieve identical results at a lower cooling rate.

The invention will now be elucidated in more detail on the basis of exemplary embodiments and the accompanying schematic drawings, in which identical reference numerals referring to similar features.

Figure 2:
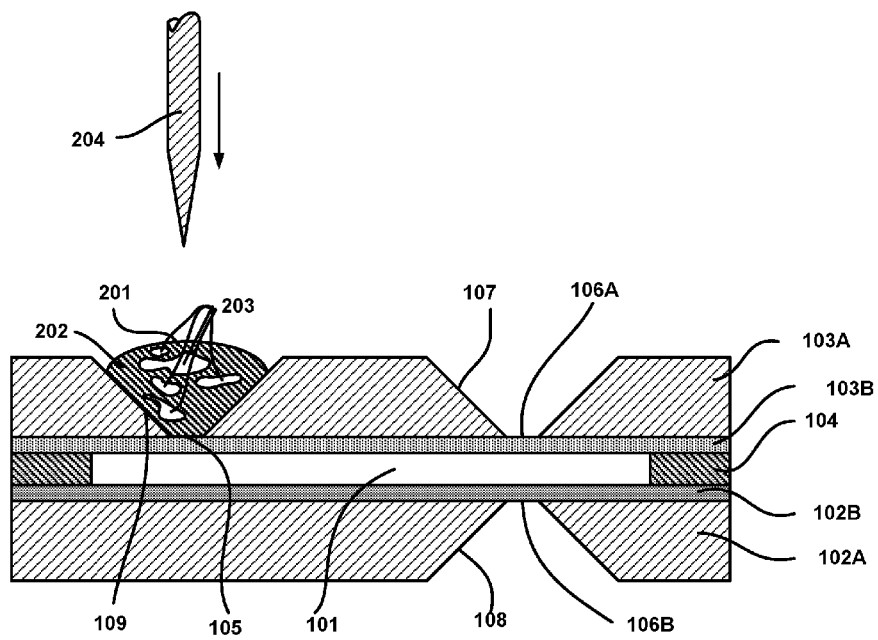
Figure 3:
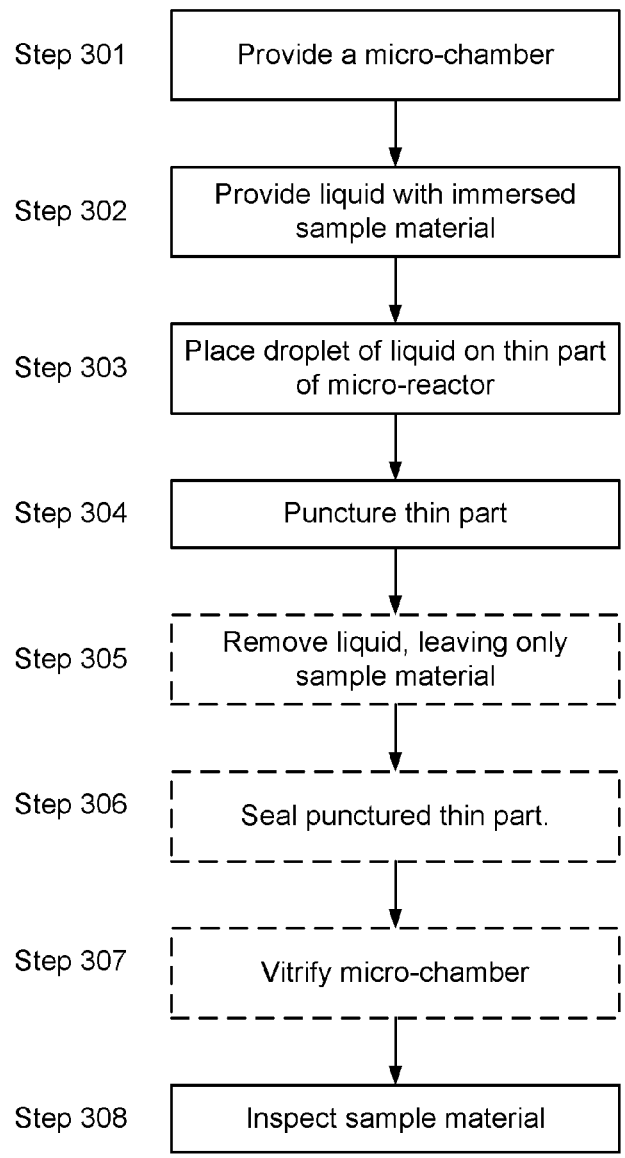

To that end:
  FIG. 1 schematically shows a micro-chamber,
  FIG. 2 schematically shows a micro-chamber at the moment that sample material is inserted,
  FIG. 3 shows a flowchart of an exemplary method using the micro-chamber.

FIG. 1 schematically shows a micro-chamber.

An inspection volume 101 is defined by a first rigid layer 102A+102B, a second rigid layer 103A+103B and a hermetic seal 104.

The first rigid layer is formed by a silicon chip 102A on which a thin layer of, for example, siliconnitride 102B is formed. In the silicon chip 102A a recess 108 is formed so that a window 106B transparent to radiation is formed. The thickness of the thin (nitride) layer as described by Mele [-2-] is 15 nm, making the window transparent to a wide range of radiation.

A second rigid layer 103A+103B is similarly formed by a silicon chip 103A on which a thin layer of, for example, siliconnitride 103B is formed. In the silicon chip 103A a recess 107 is formed so that a window 106A transparent to radiation is formed.

The second rigid layer comprises a further recess 109 so that a thin part 105 separates the inspection volume from the outside. The thin layer is easily punctured.

A hermetic seal 104 is used to bond the two chips together. When the bonding is done in a vacuum the inspection volume thus sealed is an evacuated inspection volume.

It is noted that the microchamber may comprise a multitude of windows, further structures (called 'pillars' in Creemer [-1-]) to avoid deformation ('bulging') of the siliconnitride layers, integrated heater elements to control the temperature, for example enabling inspection at elevated temperatures.

It is noted that, instead of sealing two chips back-to-back, also the process described by Mele [-2-] can be used to form the micro-chamber. The skilled person will find many modifications.

It is further noted that the rigid layer(s) need not be silicon, but may be another type of semiconductor material, or, for example, glass. The latter is especially attractive when only inspection with visible light is desired. Similarly the thin layer(s) can be formed from another material.

Polymers ('plastics') can be used for inspection using X-rays.

The seal can be an inherent part of the product formed (see Mele [-2-]), can be formed as a bond (see Creemer [-1-]), but may also take the form of an O-ring, or for example an epoxy glue.

FIG. 2 schematically shows a micro-chamber at the moment that sample material is inserted.

The micro-chamber shown and described in the paragraphs before and shown in FIG. 1, is here loaded with a droplet 201 of a liquid 202 with sample material 203. A needle 204 is ready to puncture the thin part 105, after which the droplet is sucked into the inspection volume 101.

It is noted that as an alternative to puncturing the thin part with a dedicated needle, a syringe loaded with the liquid containing the sample material can be used to puncture the thin part after said syringe applied the liquid to the recess by first squeezing a bit of liquid out while the syringe is slightly removed from the thin part and then use the syringe to puncture the thin part by moving it in the direction of the thin part (through the droplet comprising the sample material). An advantage is that the syringe for applying the liquid need not be removed to make place for a needle for puncturing.

FIG. 3 shows an exemplary method using the micro-chamber.

In step 301 a micro-chamber is provided.

In step 302 a liquid with immersed sample material is provided. The liquid with immersed sample material may be water with biological material (cells or parts thereof, enzymes, etc), and the biological material may be in its natural form, or it may be stained, marked with markers, etc. The liquid with sample material may also be a liquid with immersed solid particles, the liquid either being water or for example a solvent (alcohol, acetone, etc), and the solid particles being, for example, catalysts, grinded minerals, or such like.

In step 303 the liquid with immersed sample material is placed on the thin part of the micro-reactor.

In step 304 the thin part is punctured. Thereby the liquid is exposed to ambient pressure at one side and vacuum at the other side, resulting in the droplet to be sucked into the evacuated inspection volume.

It is noted that this step needs to be performed in an environment with a pressure substantially higher than the vacuum in the micro-chamber, for example at ambient air pressure.

As noted earlier, the puncture can be made by a dedicated needle (as shown in FIG. 1) or by a syringe used to apply the immersed sample material in the previous step.

In optional step 305 the liquid is removed, leaving only sample material in the inspection volume. Removal of the liquid may comprise warming of the micro-reactor, or placing the micro-reactor in a vacuum chamber, or at least a chamber with a reduced pressure.

In optional step 306 the puncture in the thin part is sealed. Especially when inspecting in vacuum (for example in an electron microscope) it may be necessary to close the puncture to avoid liquid evaporating and the vapor entering the vacuum chamber of the electron microscope, and/or avoiding unwanted drying of the sample material. The sealing can comprise adding bee-wax, adding a glue (for example cyanoacrylic glue), or an epoxy based resin.

In optional step 307 the micro-reactor (and thus the sample material in it) is vitrified. Vitrification in cryo-electron microscopy is the process of freezing water so quickly that no ice crystals are formed. This typically implies cooling the water at a rate of approximately $10^5$ K/s to a temperature below about 135 K. Vitrification is used in electron microscopy because radiation damage to biological samples, for example enzymes and organelles of cells, is reduced at low temperatures than at high temperatures.

In step 308 the sample material is inspected. The inspection may comprise exposing the sample material to light (visible or UV) and determine the position of structures (by optical microscopy or by fluorescence), or X-ray inspection, or inspection by electron microscopy, or combinations thereof (sequential in time or simultaneously).

It is noted that for improved inspection, a window can be formed by milling material of the micro-chamber away, e.g. using focused ion beam milling. Especially when inspecting a vitrified sample only the amorphous ice and embedded sample material are then scattering the (electron) beam.

NON-PATENT LITERATURE

-1- J. F. Creemer et al., "An all-in-one nanoreactor for high-resolution microscopy on nanomaterials at high pressures", proceeding of MEMS 2011, Cancun, Mexico, Jan. 23-27, 2011.

-2- L. Mele et al., "Wafer-level assembly and sealing of a MEMS nanoreactor for in situ microscopy", J. Micromech. Microeng. 20 (2010) 085040.

The invention claimed is:

1. A micro-chamber for inspecting sample material, the sample material immersed in a liquid when filling the micro-chamber, the micro-chamber comprising:
   an inspection volume for holding the sample material, the inspection volume defined by:
      a first rigid layer,
      a second rigid layer spaced from the first rigid layer, and
      a hermetic seal between the first and the second rigid layers,
wherein
prior to filling the inspection chamber with the liquid with immersed sample material,
   a thin part of at least one of the rigid layers separates the inspection volume from the outside,
   the thin part is equipped to be punctured, and
   the inspection volume is an evacuated volume,
as a result of which the liquid with immersed sample material, when placed upon the thin part, is sucked into the inspection volume when the thin part is punctured.

2. The micro-chamber of claim 1 in which the micro-chamber is equipped with a window transparent to radiation, as a result of which said radiation can enter and/or leave the inspection volume via this window.

3. The micro-chamber of claim 2 in which the micro-chamber is equipped with two windows transparent to radiation, one window in the first rigid layer and the second window in the second rigid layer, the windows positioned relative to each other such, that radiation entering the inspection volume via one window can leave the inspection volume via the other window, thereby enabling transmissive inspection of the sample material.

4. The micro-chamber of claim 2, in which the radiation is radiation from the group of infrared light, visible light, ultra-violet light, X-ray, energetic electrons, neutrons, and the entrance window is transparent to said radiation.

5. The micro-chamber of claim 1, in which the hermetic seal is formed by an elastomer.

6. The micro-chamber of claim 1, in which the hermetic seal is formed by bonding the first and the second rigid layer to each other.

7. The micro-chamber of claim 1 in which the first and the second rigid layer are spaced less than 10 μm from each other, preferably less than 2.5 μm.

8. The micro-chamber of claim 1 in which at least one of the two rigid layers is a semiconductor chip.

9. A method of filling a micro-chamber according to claim 1 for inspecting sample material, the method comprising:
  providing a micro-chamber according to claim 1,
  providing sample material immersed in a liquid,
  placing a droplet of the liquid with immersed sample material on the thin part of the micro-chamber,
  puncturing the thin part,
  inspecting the sample material.

10. The method of claim 9 in which, after puncturing the thin part and prior to inspection, the method comprises a step of evaporating the liquid in which the sample material is immersed.

11. The method of claim 9 in which, after puncturing the thin part and prior to inspection, the method comprises a step of sealing the puncture.

12. The method of claim 9 in which inspection of the sample material comprises exposing the sample material to radiation from the group of infrared light, visible light, ultra-violet light, X-ray, energetic electrons, neutrons, and the window through which said radiation is admitted to the sample is transparent to said radiation.

13. The method of claim 9 in which inspection of the sample material comprises detecting radiation emitted by the sample material, the radiation from the group of infrared light, visible light, ultra-violet light, X-ray, energetic electrons, neutrons, and the window through which said radiation is detected is transparent to said radiation.

14. The method of claim 9 in which after puncturing the thin part and before inspection of the sample material the method comprises a step of vitrifying the micro-chamber and the sample material in it.

15. A method of inspecting sample material, comprising:
  providing a micro-chamber, the micro-chamber comprising an inspection volume, the inspection volume being evacuated and defined by a first rigid layer and a second rigid layer spaced from the first layer, with a hermetic seal between the first and second layers, at least one of the layers having with a thin part equipped to be punctured;
  providing sample material immersed in a liquid;
  placing a droplet of liquid containing the sample material on the thin part of the micro-chamber;
  admitting liquid containing sample material to enter the micro-chamber by puncturing the thin part; and
  inspecting the sample material.

16. The method of claim 15, wherein the micro-chamber further comprises a window, the window being transparent to radiation.

17. The method of claim 16, wherein the first layer and second layers are each equipped with a window, arranged such that the sample material is placed between the windows and inspection of the sample comprises detecting radiation transmitted through the sample material.

18. The method of claim 15, wherein inspection of the sample comprises detecting radiation emitted from the sample material.

19. The method of claim 15, further comprising allowing the liquid in which the sample material is contained to evaporate before inspecting the sample material.

20. The method of claim 15, further comprising vitrifying the micro-chamber and the sample material contained within before inspecting the sample material.

* * * * *